United States Patent [19]

Hampp et al.

[11] Patent Number: 5,039,390

[45] Date of Patent: Aug. 13, 1991

[54] CHEMICALLY SENSITIVE TRANSDUCER

[76] Inventors: Norbert Hampp, Ungererstrasse 43, 8000 München 40, Fed. Rep. of Germany; Christoff Brauchle, Rotkäppchenstrasse 89A, 8000. München 83, Fed. Rep. of Germany

[21] Appl. No.: 466,303

[22] PCT Filed: Aug. 9, 1989

[86] PCT No.: PCT/DE89/00525

§ 371 Date: May 4, 1990

§ 102(e) Date: May 4, 1990

[87] PCT Pub. No.: WO90/01694

PCT Pub. Date: Feb. 22, 1990

[30] Foreign Application Priority Data

Aug. 11, 1988 [DE] Fed. Rep. of Germany ....... 3827314

[51] Int. Cl.$^5$ ............................................. G01N 27/30
[52] U.S. Cl. .................... 204/412; 204/416; 357/25
[58] Field of Search .................... 357/25; 204/416, 412

[56] References Cited

U.S. PATENT DOCUMENTS

| | | | |
|---|---|---|---|
| 4,020,830 | 5/1977 | Johnson et al. | 128/635 |
| 4,133,735 | 1/1979 | Afromowitz et al. | 357/25 X |
| 4,180,771 | 12/1979 | Guckel | 357/25 X |
| 4,385,274 | 5/1983 | Shimada et al. | 324/71.6 |
| 4,437,969 | 3/1984 | Covington et al. | 204/403 |
| 4,449,011 | 5/1984 | Kratochvil et al. | 174/52 PE |
| 4,505,799 | 3/1985 | Baxter | 204/416 |
| 4,508,613 | 4/1985 | Busta et al. | 204/418 |
| 4,514,276 | 4/1985 | Covington et al. | 204/415 |
| 4,921,591 | 5/1990 | Mochizuki et al. | 204/412 |

FOREIGN PATENT DOCUMENTS

| | | |
|---|---|---|
| 0012035 | 6/1980 | European Pat. Off. . |
| 0065350 | 11/1982 | European Pat. Off. . |
| 0078590 | 5/1983 | European Pat. Off. . |
| 0174712 | 3/1986 | European Pat. Off. . |

Primary Examiner—John F. Niebling
Assistant Examiner—Arun S. Phasge
Attorney, Agent, or Firm—Evenson, Wands, Edwards, Lenahan & McKeown

[57] ABSTRACT

A chemically sensitive transducer for selectively determining a chemical property of a fluid and providing a measurement signal to an amplifying circuit. The transducer has a measuring electrode coupled to the amplifying circuit and provides a measurement signal to the amplifying circuit. A membrane covers the measuring electrode, this membrane being sensitive to a specified chemical property. A carrier plate, with first and second sides, has the measuring electrode arranged on its first side and the amplifying circuit on its second side. The carrier plate has a conductor extending between the first and second sides which electrically couples the measuring electrode and the amplifying circuit.

16 Claims, 3 Drawing Sheets

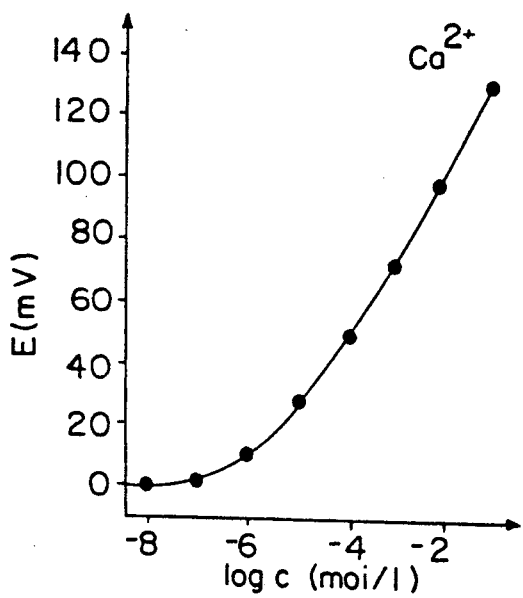
FIG. 6-I
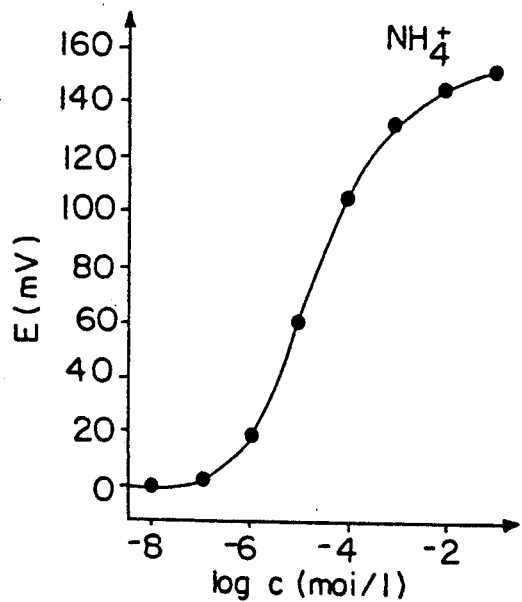
FIG. 6-II
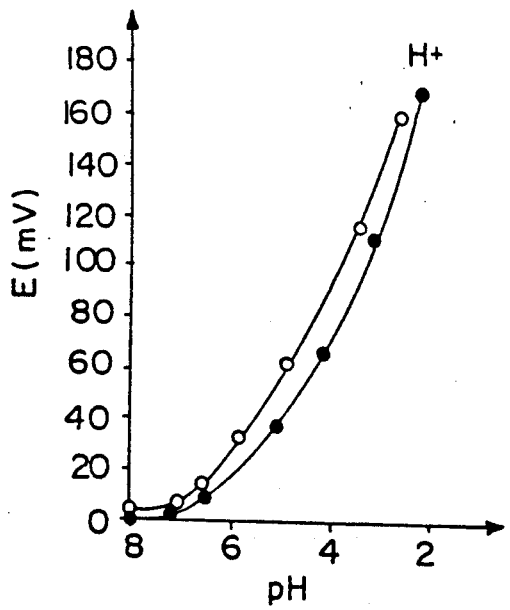
FIG. 6-III
| SENSITIVITY | H+ | Ca²⁺ | NH₄⁺ |
|---|---|---|---|
| RISE (mV/DECADE) | 42 | 28 | 49 |
| RESPONSE TIME (sec) | <10 | <10 | <10 |
FIG. 6-IV

CHEMICALLY SENSITIVE TRANSDUCER

BACKGROUND AND SUMMARY OF THE INVENTION

The present invention relates to a chemically sensitive transducer for the selective detection of the chemical properties of a fluid, and more specifically, to a transducer with a measuring electrode overlaid with a membrane that is sensitive to the chemical properties. This electrode is coupled to the gate of a field-effect transistor. The transducer has an encapsulation which isolates the entire transducer except for the membrane from the fluid.

The term "chemically sensitive" refers to an ion or gas sensitive property, a sensitivity to enzyme substrates, to antibodies/antigens or to hydride-forming DNA/RNA groups. Depending on their sensitivity, transducers can be utilized in medicine, for example in blood analysis, in clinical chemistry, for therapy control, hormone determination, infection and tumor diagnoses, as well as in fermentation control, food and environment analyses and process control.

A chemically sensitive transducer is known from EP-B-0 065 350, in which the gate of a field-effect transistor is connected via a laterally abutting conductor to an allocated measuring electrode disposed on the same side of the substrate. The field-effect transistor is provided in a semiconductor substrate. The measuring electrode is provided with a membrane, (i.e., a coating) which is sensitive to the chemical property to be determined and which is applied by electroplating, sputtering or vapor deposition. The field-effect transistor is encapsulated against the fluid that is to be examined by a protective layer composed of an epoxin resin or rubber.

Immersing a transducer of this design in the fluid to be examined yields, due to the ion exchange reactions between the electro-active substance of the membrane and the fluid at the gate electrode of the field-effect transistor, a potential which influences the channel conductivity of the field-effect transistor. Potentiometric or ammetric measurement permits obtaining a corresponding output signal proportional to the concentration of the parameter to be measured.

Other chemically sensitive transducers are known from EP-A-0 302 228, EP-B 0 078 590 and U.S. Pat. No. 4,514,276.

Although the voltage produced by the ion exchange reaction lies in the mV range, the non-reactive load capacity of the membrane, however, lies in the pA to fA range. When working with such low charge quantities, it is important that all interfering influences, in particular those of an electric or thermal nature, be prevented, a point for which the above-cited publications provide no measures. Another problem with the known transducers is that they can only be utilized for the determination of those chemical properties to which the membranes, which can be applied onto the measuring electrode with the aforementioned processes, are sensitive.

An object of the present invention is to provide a chemically sensitive transducer featuring higher sensitivity in comparison to known chemically sensitive transducers and which, at the same time, is insensitive to electric influences and temperature fluctuations. The transducer should also be able to be designed to be sensitive to properties that can be detected only with membrane substances of little stability.

These and other objects are provided by the present invention which provides a chemically sensitive transducer for selectively determining a chemical property of a fluid and providing a measurement signal to an amplifying circuit. The transducer has a measuring electrode coupled to the amplifying circuit and provides a measurement signal to the amplifying circuit. A membrane covers the measuring electrode, this membrane being sensitive to a specified chemical property. A carrier plate, with first and second sides, has the measuring electrode arranged on its first side and the amplifying circuit on its second side. The carrier plate has a conductor extending between the first and second sides which electrically couples the measuring electrode and the amplifying circuit.

The arrangement of the measuring electrode and the amplifying circuit on the opposite sides of a carrier plate with contact being made through the carrier plate yields, with small overall transducer dimensions and unrestricted possible design with regard to the size and number of measuring electrode surfaces, the shortest distances between the measuring electrode and the corresponding amplifying circuit with an accordingly high signal/noise ratio. In this manner, the transducer of the present invention increases its sensitivity in comparison to conventional transducers. Furthermore, a largely free choice in the design of the measuring problems is allowed by the present invention. In particular, all types of membranes, such as those used with conventional ion-selective electrodes, can be utilized.

Furthermore, the amplifying circuit can also be designed with very different techniques. For example, the transducer can be realized cost-effectively even in small quantities with the hybrid technique or thin film technique.

In an embodiment of the invention, the carrier plate consists of an insulating material, which may be, for example $SiO_2$, a ceramic material such as $Al_2O_3$, glass, an epoxy resin or a plastic material. In this manner, the carrier plate not only ensures required stability, where there is little thickness, but also shields the amplifying circuit reliably from environmental influences. A ceramic material is suited, for example, for application of the measuring electrode material, the conducting layer and other conductor channels with the thick film technique.

In an embodiment of the invention, a conducting layer is arranged between the amplifying circuit and the carrier plate, which can be used at the same potential as the measuring electrode. This results in active shielding of the high impedance input signal from electric interference fields, thereby further improving the signal/noise ratio, and reducing the limit of sensitivity of the transducer and raising its speed of response as well as improving cross-talk behavior in a transducer with several channels. Further input capacitances are substantially eliminated.

In an embodiment of the invention, the electric connection (the conductor) between the measuring electrode and the field-effect transistor in the amplifying circuit is provided by a borehole extending completely through the carrier plate. This borehole preferably has a diameter of less than 0.1 mm and is coated at least on its sidewalls with a conducting material. This embodiment of the present invention has the advantage that, because of the small cross-section of the borehole, stationary or weakly moving fluids can not reach the amplifying circuit due to their surface tension even if the opening of the borehole were uncovered.

In an embodiment of the invention, the measuring electrodes, the conductor running through the carrier plate and if required, the conducting layer, are made of a material which is chemically inert to the fluid to be examined, so that it does not react with the fluid. In particular, practically any adjuvants (solvents, reducing and oxidating agents, radicals for couplings and polymerizings) may be employed for applying the membrane. Such materials are, by way of illustration, gold, platinum, silver, palladium (or their alloys) or a conductive polymer, such as polypyrrol.

In an embodiment of the invention, a mask plate disposed on the carrier plate restricts the area of the measuring electrode. This has the advantage that a trough-like receptacle with a defined base area is formed for applying the membrane onto the measuring electrode so that there is a corresponding expansion in the membrane and its thickness can be determined by simple dosing of the fluid. In this manner, it also becomes possible for the user himself to lay on the membrane with sufficient precision, which is necessary when sensitive materials and materials of little biological stability such as enzymes and antibodies are to be employed as membranes. Furthermore, it becomes possible to reuse transducers by removing spent membranes and replacing them with new ones. Membranes that can be put on by the user can be applied by means of electrochemical reactions or in a dissolved state. Furthermore, the mask plate may also be removable and therefore is replaceable. The mask plate may be arranged on the transducer only for the purpose of applying the membrane or the membrane surface may be varied by disposing mask plates of different design.

In an embodiment of the invention, the mask plate covers the borehole. This is useful for additional protection of the amplifying circuit provided in the encapsulment.

In an embodiment of the invention, an insulating layer covers the borehole, this insulating layer being provided between the mask plate and the carrier plate. The insulating layer further seals the conductor running through the carrier plate. The insulating layer may be made of $SiO_2$, polyamide, epoxy resin, aluminum oxide or a silicon resin.

In an embodiment of the invention, the mask plate and the covering encapsulating the amplifying circuit are also made of the same material as the carrier plate. In this way, mechanical tension, like that which can lead to leakage due to temperature fluctuations at different thermal expansion coefficients, can be avoided. Furthermore, a ceramic makes a good electric insulator and is chemically inert, i.e. it does not react with the fluid to be examined and is physiologically indifferent.

The high pressure filling of the transducer encapsulation with an inert gas, as provided in an embodiment of the invention, is an additional measure that protects the amplifying circuit against penetration of water vapor and prevents oxidation of the electronic components, for example in autoclaving processes as can be conducted with temperature stable sensors.

In an embodiment of the invention, the transducer is provided with at least one pair of differential sensors having an active measuring electrode and an inactive measuring electrode. This circumvents the necessity of having an external reference electrode, which, however, can be employed at any time with the transducer of the present invention. The sensor channels in each case comprise a pair of sensors, the potential of which is determined in relation to a reference dissolving contact and are subtracted from one each other. One electrode surface is covered with the desired membrane and the other with the same, but "carrier-free" mixture. The term "carrier-free" means that the membrane, or the layer, does not have the sensitive component. Due to the formation of a differential, the instability of the potential of the reference dissolving contact and the unspecified matrix effect of the membranes like that produced, for example, by the diffusion of lipophile blood fats, is eliminated.

Other objects, advantages and novel features of the present invention will become apparent from the following detailed description of the invention when considered in conjunction with the accompanying drawings.

BRIEF DESCRIPTION OF THE DRAWINGS

FIG. 6 illustrates exemplary characteristic curves of the transducer of the present invention.

DETAILED DESCRIPTION OF THE DRAWINGS

Figure 1:
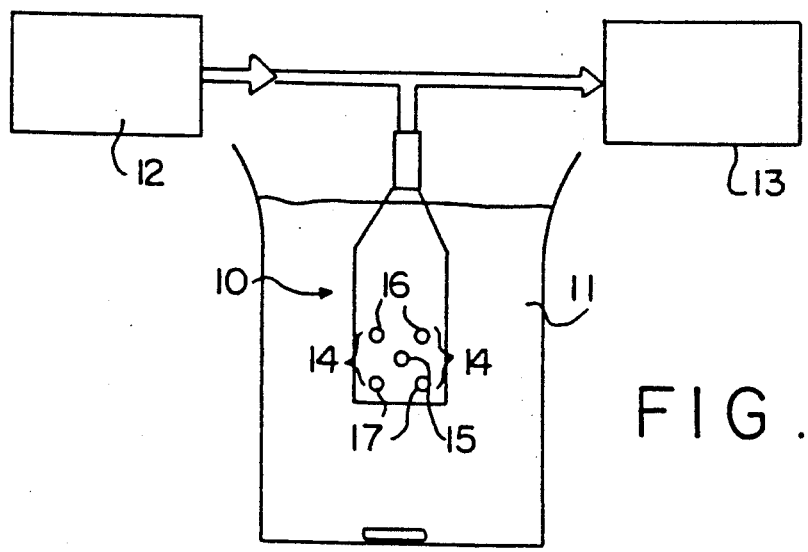
FIG. 1 shows a schematic representation of a chemically sensitive transducer constructed in accordance with an embodiment of the present invention.

In the embodiment of the invention depected in FIG. 1, a chemically sensitive transducer 10 is immersed in a fluid 11 that is to be examined. The transducer 10 is coupled via external supply lines to a voltage supply 12 and an indicator device 13, which may, for example, be a curve-plotting recorder.

The transducer 10 is provided with two pairs of differential sensors 14 and a reference dissolving contact 15 on the surface facing the viewer in FIG. 1. Each pair of differential sensors 14 contains an active sensor 16 and a passive sensor 17. The active and the passive sensor of each pair of differential sensors 14 are disposed symmetrically in relation to the reference dissolving contact 15.

Figure 2:
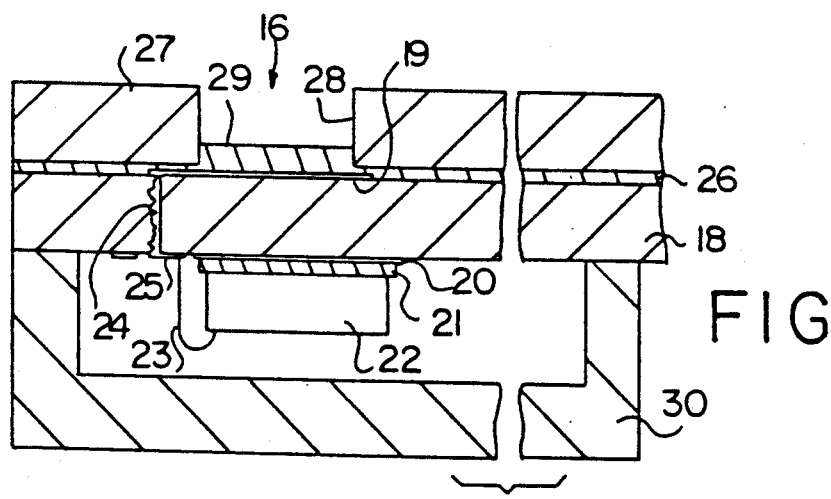
FIG. 2 is a partial longitudinal section through the transducer of FIG. 1.

The partial sectional view representation of FIG. 2 illustrates the electronics of one of the active sensors 16 in more detail. The sensor 16 comprises a measuring electrode 19 on the top side of a carrier plate 18 made of $Al_2O_3$. On the bottom side of the carrier plate 18, opposite the measuring electrode 19, is a conducting layer 20.

An amplifying circuit 22 is arranged on the conducting layer 20 with a $SiO_2$ insulating coat 21 inserted between the conducting layer 20 and the circuit 22. This amplifying circuit 22 can be a commercial integrated circuit, examples of which shall be briefly described briefly later with reference to FIGS. 4 and 5.

The gate of an input field-effect transistor of the amplifying circuit 22 is coupled to the measuring electrode 19 via a wire 23 and a conductor 24, making contact all the way through the carrier plate 18. The conductor 24 runs through a micro-borehole completely through the carrier plate 18. This micro-borehole can be laser machined to have a diameter in the range of less than 0.1 mm. In order to produce the measuring electrode 19 and the conducting layer 20, the surface of the carrier plate 18 is coated on the appropriate areas with a gold pressure paste, with which the micro-borehole is filled at the same time. When the pressure paste is fired, a conducting gold coat forms on the sidewalls of the micro-borehole.

Figure 3:
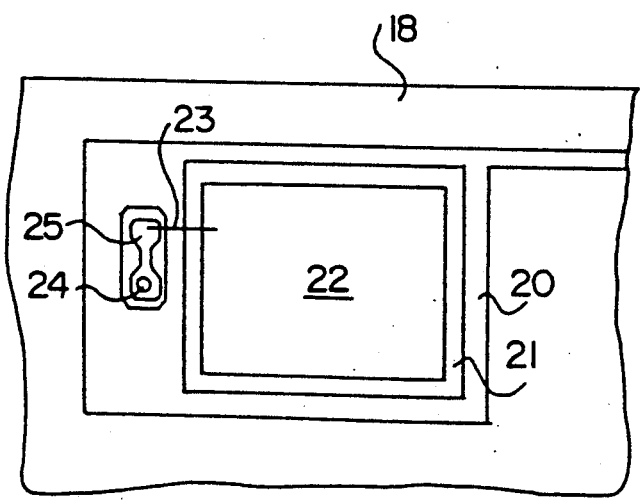
FIG. 3 is a top view of the area bearing the amplifying circuit of the carrier plate depicted in FIG. 2.

FIG. 3 shows the special form of conducting layer 20, the $SiO_2$ insulating coat 21 applied on it and the integrated amplifying circuit 22 arranged on top of that. In a recess of the conducting coat 20, the conductor 24 running through the micro-borehole terminates in a contact pad 25 to which the bonding wire 23 is affixed.

Referring back to FIG. 2, an $SiO_2$ layer 26 is adjacent to the top side of the carrier plate 18. A mask plate 27 made of $Al_2O_3$ ceramic is provided on top of this $SiO_2$ layer 26. The mask plate 27 has a sensor opening 28 in the region of the measuring electrode 19. The micro-borehole, containing the conductor 24, is outside of this sensor opening 28 and is therefore covered by the mask plate 27 and is additionally sealed by the $SiO_2$ layer 26. In the region of the sensor opening 28, the measuring electrode 19 is coated with a membrane 29, which contains a substance that is sensitive to the specific chemical property to be detected.

As can be seen in FIG. 2, the sensor 28 in the mask plate 27 forms in conjunction with the measuring electrode 19 a trough-like indentation with a defined base area. The membrane 29 can therefore be very easily applied in a fluid form, whereby a predosed amount of fluid yields a membrane of predetermined thickness. Due to this design, the application of membrane 29 may be left to the user and may occur shortly before actual utilization of the sensor, which is of significance in the case of short-lived substances. Furthermore, this mode of application is also suited for sensitive materials, which cannot be applied with conventional procedures like sputtering or vapor deposition. The use of mask plates 27, which can be ceramic, for example, permits removing the spent membrane 29 and replacing it with a new one so that as a whole the transducer 10 can be used repeatedly.

Principally, a passive sensor 17 does not differ in design from the active sensor 16 described in FIG. 2. It also has a membrane, which is of the same composition as that of the active sensor 16 except for the sensitive component, which makes up about 1% of the membrane mass in the membrane 29 of the active sensor 16.

The reference dissolving contact 15 depicted in FIG. 1, on the other hand, differs from the design shown in FIG. 2 in that in it the measuring electrode 19 is not covered with a membrane 29 and is not provided with its own circuitry. The reference dissolving contact 15, which provides a reference potential for the entire transducer 10, is coupled to the amplifying circuit 22 in a manner described later.

In the embodiment according to FIG. 2, the measuring electrode 19 and the conducting layer 20 with the ceramic carrier plate 18 between the two form a capacitor. This capacitor effects a small transducer input capacitance and shielding of the high impedance input signal (in the range of $10^{15}\Omega$) against stray electric fields.

The sensor 16 has a covering 30, which in conjunction with carrier plate 18 encapsulates the amplifying circuit 22 disposed on the bottom side of the carrier plate 18. The covering 30 is also composed of $Al_2O_3$ ceramic in the embodiment of FIG. 2. The space within the encapsulation is filled under pressure with an inert gas in order to counteract penetration of vapor from outside and to prevent oxidation of the electrical components under the influence of temperature. The covering 30 may extend over the entire rear side of the transducer 10 depicted in FIG. 1 so as to encompass the electronics of all the sensors 16, 17.

Due to the fact that the transducer 10 can be fitted with two or more pairs of differential sensors 14, two or more chemical properties of the fluid can be determined simultaneously by choosing the selective substances of the active sensors 16.

Figure 4:
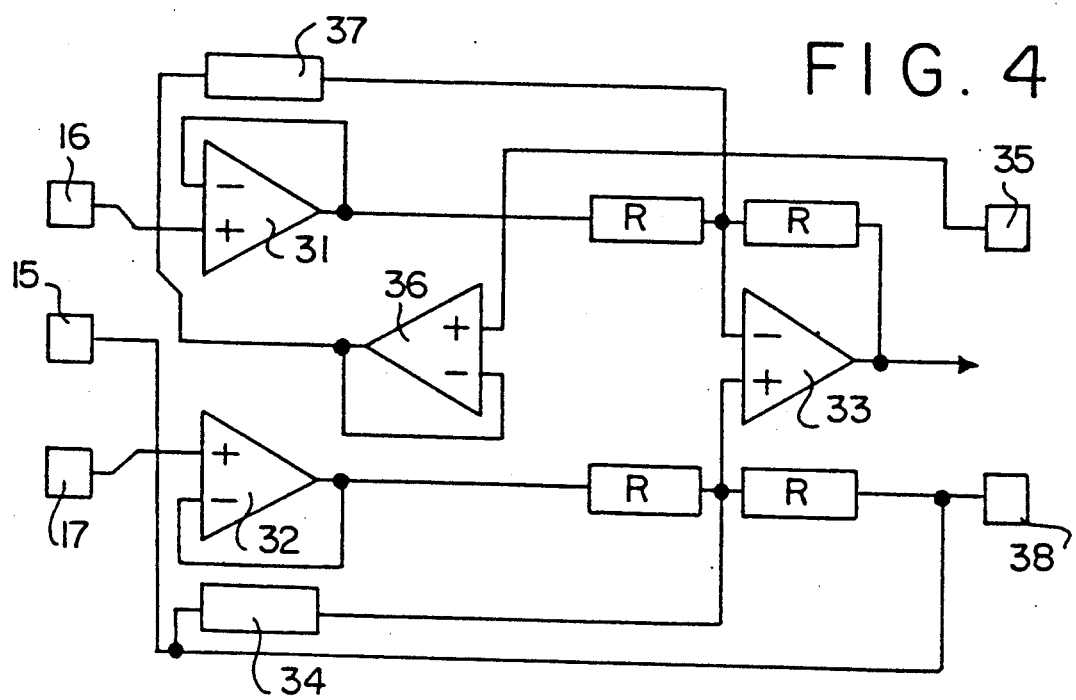
FIG. 4 shows an embodiment of an electric circuit for potentiometric signal detection.

FIG. 4 shows a circuit for potentiometric signal detection in which the active sensor 16 is coupled to the input field-effect transistor of a first operational amplifying stage 31, and the passive sensor 17 is coupled to the input field-effect transistor of a second operational amplifier 32. Very high ohmic primary stages ($R_{in} \approx 10^{15}\Omega$, $I_{in} \approx 150$ fA) are used for the impedance conversion of the electrode potential. The low impedance output signals of the amplifiers 31 and 32 are transmitted to the two inputs of a differential amplifier 33, the output signal of which forms the measurement signal. The reference dissolving contact 15 is coupled via a resistance 34 with the input, to which the signal from the passive sensor 17 is transmitted, of the differential amplifier 33. A trimming input 35 is coupled via a third operational amplifier 36 followed by another resistance 37 to the input, to which the output signal of the active sensor 16 is also transmitted, of the differential amplifier 33. The reference dissolving contact 15 is connected to an analog ground terminal 38 of the transducer. For potentiometric operation, the conducting layer 20 is connected to the output of one of the operational amplifiers 31, 32 so that the impedance converted input signal is provided on the shielding surface.

The circuit depicted in FIG. 4 is an example of the amplifier circuit 22 of FIG. 2 in an integrated form.

Figure 5:
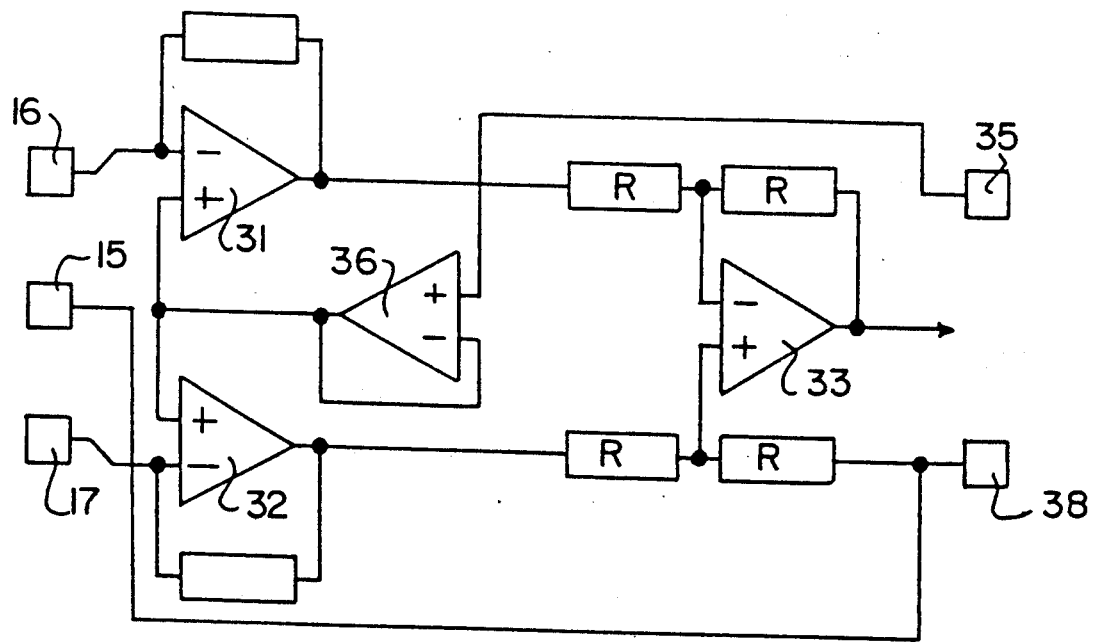
FIG. 5 shows an embodiment of an electric circuit for ammetric signal detection.

The circuit according to FIG. 5 is designed for ammetric signal detection, with the same designations referring to the same circuit elements as in FIG. 4. The difference in wiring is apparent when compared with FIG. 4.

In contrast to conventional electrodes, the transducer 10 of the present invention permits miniaturizing the measuring system and the membrane surface 29 while having largely variable dimensions and shape. The transducer 10 requires low fabrication and development costs and may be designed for a great variety of different applications. The sensors 15, 16, 17 have short response times. A transducer 10 provided with several sensors permits measuring several parameters simultaneously. An embodiment that employs several membranes with different selectivities makes it possible to largely eliminate electronically cross-selectivities of individual pairs of differential sensors. Signal detection is integrated in the transducer in such a manner that the output signal can be utilized as an indicator without any additional processing.

Compared to conventional chemically sensitive field-effect transistors, the transducer 10 of the present invention presents no durability problems due to its encapsulation. A great variety of different membrane substances can be easily applied, and there is high variability in combining the bioselective components. Due to the fact that larger electrode surfaces are possible, the amount of the membrane substance to be applied can be reproduced more accurately. Diffusion problems, like those occurring with FET multi-sensors, are avoided.

FIG. 6 shows exemplary characteristic curves of an embodiment of the sensor of the present invention for various ions. In this example, the electrode surfaces are sensitized with fluid PVC membranes although other known membrane mixtures may be used for this purpose. In accordance with the differential concept, a carrier containing membrane and a carrier-free membrane are employed for each type of ion.

In order to apply the membranes 29 onto the surface of the electrodes 19, the following procedure is followed. After drying the sensors over $CaCl_2$, 7 liters of a 21% solution of PVC membrane in THF are dripped with a pipette into the respective electrode trough. After the THF has vaporized, this procedure is repeated. Subsequently, the membranes are conditioned in an electrolyte mixture.

The geometry of the sensor zone is exactly defined by the electrode mask so that reproduceable membranes 29 of the same thickness can be produced by simply dosing the fluid. As the membranes 29 are affixed to the surface of the electrode 19 by means of adhesion, they can be removed and the sensor module can be recoated after cleaning.

The following table illustrates the composition of the sensitive membranes for the ions given, by way of example, in FIG. 6. The membrane compositions correspond to the mixtures described in connection with classical ion-selective electrodes. The differential membranes differ from the sensitive membranes by the lack of the carrier.

| Sensitivity | Carrier | Matrix | Plasticize | Additive |
| --- | --- | --- | --- | --- |
| $Ca^{2+}$ | ETH 1001 1% | PVC 66% | oNPOE 33% | — |
| $NH_{4+}$ | nonactin 1% | PVC 66% | TEHP 33% | — |
| $H^+$ | ETH 1907 1% | PVC 66% | oNPOE 33% | — |

TEHP = tris (2-ethylhexyl)-phosphate
oNPOE = ortho-nitrophenyloctylether

In FIG. 6, the response curves of the sensors 16, 17 of the present invention are given for calcium ions in section (I), in section (II) for ammonia ions, and in section (III) for protons. The response curves in sections I and II are for aqueous solutions of chloride salts, the response behavior of the proton sensor is given for 500 nM (black dotted points of measurement) and for 50 mM (white dotted points of measurements) of sodium phosphate buffer solution. In section (IV) are compiled the response times and the gradients determined in the linear range of the sensors.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. A chemically sensitive transducer for selectively determining a chemical property of a fluid and providing a measurement signal to an amplifying circuit that contains a field-effect transistor, comprising;
    a measuring electrode coupled to the amplifying circuit and providing a measurement signal to the amplifying circuit;
    a membrane covering said measuring electrode, said membrane being sensitive to a specified chemical property;
    a carrier plate composed of an insulating material and having first and second sides, with said measuring electrode being arranged said first side and the amplifying circuit being arranged on said second side, said carrier plate including a conductor extending between said first and second sides, said conductor electrically coupling said measuring electrode to the amplifying circuit; and
    means for encapsulating the transducer to isolate said transducer from the fluid except for said membrane.

2. A transducer according to claim 1, wherein said insulating material is one of: $SiO_2$; a ceramic material; $Al_2O_3$; glass; an epoxy resin; and a plastic material.

3. A transducer according to claim 2, further comprising a conducting layer between said carrier plate and the amplifying circuit, said conducting layer being arranged opposite said measuring electrode.

4. A transducer according to claim 3, wherein said conductor is a borehole running completely through said carrier plate and having a diameter of less than 0.1 mm, said borehole being coated at least on its sidewalls with a conducting material.

5. A transducer according to claim 4, wherein said measuring electrode, said conductor and said conducting layer are compared of a material which is chemically inert to the fluid whose chemical property is selectively determined.

6. A transducer according to claim 5, wherein said material is one of: gold, platinum silver, copper, palladium, or alloys thereof or a conductive polymer.

7. A transducer according to claim 6, further comprising a mask plate on said carrier plate, said mask plate restricting the area of said measuring electrode.

8. A transducer according to claim 7, wherein said mask plate covers said borehole.

9. A transducer according to claim 7, further comprising an insulating layer covering said borehole and interposed between said mask plate and said carrier plate.

10. A transducer according to claim 9, wherein said insulating layer is composed of one of the following: $SiO_2$, polyimide, epoxy resin, aluminum oxide or a silicone resin.

11. A transducer according to claim 10, wherein said mask plate is removable.

12. A transducer according to claim 1, wherein said membrane is a membrane that is applicable by electrochemical reactions or in a dissolved form.

13. A transducer according to claim 7, wherein said carrier plate, said mask plate and said means for encapsulating are composed of the same insulating material.

14. A transducer according to claim 13, wherein a space encompassing the amplifying circuit and enclosed by the combination of said carrier plate and the means for encapsulating is filled under pressure with an inert gas.

15. A transducer according to claim 1, wherein said transducer includes at least one pair of differential sensors having an active measuring electrode and an inactive electrode.

16. A chemically sensitive transducer for selectively determining a chemical property of a fluid and providing a measurement signal to an amplifying circuit that contains a field-effect transistor, comprising:

A measuring electrode coupled to the amplifying circuit and providing a measurement signal to the amplifying circuit;

a membrane covering said measuring electrode, said membrane being sensitive to a specified chemical property;

a carrier plate composed of an insulating material and having first and second sides, with said measuring electrode being arranged on said first side and the amplifying circuit being arranged on said second side, said carrier plate including a borehole extending between said first and second sides, said borehole including a conductor extending between said first and second sides, said conductor electrically coupling said measuring electrode to the amplifying circuit; and means for encapsulating the transducer to isolate said transducer from the fluid except for said membrane.

* * * * *